United States Patent
Tsutsumi

(10) Patent No.: US 9,642,813 B2
(45) Date of Patent: May 9, 2017

(54) METHOD FOR PRODUCING SOFT CAPSULE TYPE EXTERNAL PREPARATION, SOFTENING LIQUID, AND SOFT CAPSULE TYPE EXTERNAL PREPARATION

(71) Applicant: Hibiki Tsutsumi, Osaka (JP)

(72) Inventor: Hibiki Tsutsumi, Osaka (JP)

(73) Assignee: SANSHO KAKEN KABUSHIKI KAISHA (JP)

( * ) Notice: Subject to any disclaimer, the term of this patent is extended or adjusted under 35 U.S.C. 154(b) by 0 days.

(21) Appl. No.: 14/900,637

(22) PCT Filed: Jun. 25, 2013

(86) PCT No.: PCT/JP2013/067424
§ 371 (c)(1),
(2) Date: Dec. 22, 2015

(87) PCT Pub. No.: WO2014/207829
PCT Pub. Date: Dec. 31, 2014

(65) Prior Publication Data
US 2016/0151294 A1    Jun. 2, 2016

(51) Int. Cl.
| | | |
|---|---|---|
| *A61K 9/48* | (2006.01) | |
| *A61K 8/365* | (2006.01) | |
| *A61K 8/55* | (2006.01) | |
| *A61K 8/11* | (2006.01) | |
| *A61Q 19/00* | (2006.01) | |
| *A61K 8/44* | (2006.01) | |
| *A61K 8/73* | (2006.01) | |

(52) U.S. Cl.
CPC .............. *A61K 9/4883* (2013.01); *A61K 8/11* (2013.01); *A61K 8/365* (2013.01); *A61K 8/44* (2013.01); *A61K 8/55* (2013.01); *A61K 8/733* (2013.01); *A61K 9/4816* (2013.01); *A61K 9/4891* (2013.01); *A61Q 19/00* (2013.01)

(58) Field of Classification Search
CPC . A61K 8/365; A61K 8/55; A61K 8/11; A61Q 19/00
USPC .................. 424/401, 463; 514/779; 562/560
See application file for complete search history.

(56) References Cited

FOREIGN PATENT DOCUMENTS

| | | |
|---|---|---|
| JP | H02117610 A | 5/1990 |
| JP | H03109312 A | 5/1991 |
| JP | H0592909 A | 4/1993 |
| JP | H05228218 A | 9/1993 |
| JP | H08175932 A | 7/1996 |
| JP | H1129433 A | 2/1999 |
| JP | 2010043047 A | 2/2010 |
| JP | 2011074001 A | 4/2011 |
| JP | 2011074002 A | 4/2011 |
| JP | 2013139419 A | 12/2011 |

*Primary Examiner* — Yanzhi Zhang
(74) *Attorney, Agent, or Firm* — Bacon & Thomas, PLLC

(57) ABSTRACT

The invention is to provide a method for producing a soft capsule type external preparation (and a softening liquid (L) used for the production thereof, and an external preparation composed of such a capsule body (C)) which can be stably stored and leaves no film residues when rubbed with the finger when used as an external preparation although the external preparation is structured only as a capsule body (C) substantially having no external solution. An original capsule body (c) in which at least the external surface region inside an alginate capsule is present in the form of a polyvalent metal alginate is contacted with a softening liquid (L) composed of an aqueous solution comprising both "a basic amino acid (1)" and "an acid (2) selected from an organic acid or a phytic acid," thereby impregnating the softening liquid (L) into the original capsule body (c) to obtain the capsule body (C).

4 Claims, No Drawings

METHOD FOR PRODUCING SOFT CAPSULE TYPE EXTERNAL PREPARATION, SOFTENING LIQUID, AND SOFT CAPSULE TYPE EXTERNAL PREPARATION

TECHNICAL FIELD

The present invention relates to a method for producing a soft capsule type external preparation composed of an alginate capsule body (C) which does not leave any residues and easily becomes creamy when rubbed with a fingertip. In addition, the present invention relates to a softening liquid (L) used for producing the soft capsule type external preparation. Furthermore, the present invention relates to a soft capsule type external preparation composed of such a capsule body (C). The term "external preparation" indicates a cosmetic, a quasi-drug, a care product, or the like.

BACKGROUND ART

Recently, as external preparations such as cosmetics, external preparations formed by soft capsules (soft capsule bodies having a small spherical shape) come onto the market and draw attention. The reason for this is that the soft capsule has features that an effective ingredient can be stably contained therein, soft feeling is popular, and a high grade is achieved, for example.

In addition, among the external preparations formed by soft capsules, for example, the following patent applications have been made as an example which is contrived such that an external preparation is easily broken by rubbing at the time of applying the external preparation to skin and residues or a film thereof does not remain.

(Patent Document 1)

In JP 11-29433 A (Patent Document 1, JP 3151169 B1) relevant to the patent application of the present applicant, there is described "a capsule-containing cosmetic in which "a barium alginate-based capsule A," which is formed by alginate to be a spherical body and in which at least a part of alginate present at a surface side or the surface side and an inner side of the spherical body is present in the form of a polyvalent metal salt containing a barium salt, is present in "an external solution B composed of an aqueous solution of a pH-adjusted carboxy vinyl polymer." The reason why the pH-adjusted carboxy vinyl polymer is caused to be present in the external solution B is that the barium alginate-based capsule A is caught in a three-dimensional network of the carboxy vinyl polymer in the external solution B so as to make the capsule A not to be precipitated or not to be floated (Paragraph [0058]).

In this Patent Document 1, there is described a method for producing a capsule-containing cosmetic, in which the aqueous solution of the carboxy vinyl polymer is mixed with the barium alginate-based capsule A and a pH adjuster at the same time or in an arbitrary order, and the barium alginate-based capsule A is caused to be present in the external solution B composed of the aqueous solution of the pH-adjusted carboxy vinyl polymer. Here, as the pH adjuster used when pH of the aqueous solution of the carboxy vinyl polymer is adjusted, there is a description that "Sodium hydroxide is particularly preferable, but in addition to this, sodium carbonate, sodium bicarbonate, triethanolamine, diethanolamine, monoethanolamine, L-arginine, DL-alanine, sodium citrate, sodium hydrogen citrate, sodium malate, sodium tartrate, sodium malonate, sodium lactate, sodium oxalate, sodium polyacrylate, or the like can also be used." (Paragraph [0032]). Incidentally, in Example 1, Comparative Example 1, and Example 2 of this Patent Document 1, pH of the aqueous solution of 1% by weight of carboxy vinyl polymer is 3, but pH adjustment is performed by addition of an aqueous solution of potassium hydroxide such that pH of the external solution B is adjusted to 6.0 or 6.5 (Paragraphs [0044], [0049], and [0053]). That is, since pH of the aqueous solution of 1% by weight of carboxy vinyl polymer is as low as 3, pH adjustment is performed by addition of an alkaline substance.

(Patent Document 2)

In JP 5-92909 A (Patent Document 2, JP 2798224 B1) relevant to the patent application of the present applicant, there is described a cosmetic in which a caviar-shaped capsule A in which only a surface portion is formed by a film and which is easily broken by rubbing is caused to be present in a liquid agent B. The capsule A is obtained by adding a dropping liquid composed of sodium alginate and another water-soluble aqueous solution dropwise to a receiving liquid of a water-soluble calcium salt or the like. Attention is paid so that the caviar-shaped capsule A which is easily broken by rubbing is obtained by setting a concentration of sodium alginate of the dropping liquid or a concentration of the water-soluble calcium salt of the receiving liquid at the time of obtaining the capsule A to an appropriate concentration. Then, the capsule A obtained in this way is caused to be floated or precipitated in the liquid agent B such as water, saline solution, emulsion, or skin toner (Paragraphs [0028], [0029], and [0038]).

(Patent Document 3)

In JP 5-228218 A (Patent Document 3) relevant to the patent application of the present applicant, there is also described a care product including: a capsule container 1 accommodating a pearl-shaped capsule A, which is obtained in the same manner as in the above Patent Document 2 and is easily broken by rubbing, in a container provided with an extraction mechanism in a state where the capsule A is swollen by a liquid agent B; and a compact massaging tool 2 by which stimulation is given to the vicinity of an eye.

(Patent Document 4)

In JP 8-175932 A (Patent Document 4) relevant to the patent application of the present applicant, there is described a foundation cosmetic obtained by accommodating, in a container, a mixture of a foundation capsule which is composed of a composition having a powder material for foundation as an effective ingredient and is easily broken by rubbing and in which only a surface portion is formed by a film (in Paragraph [0040], sodium alginate is used), a small caviar-shaped moisturizer capsule which is composed of a composition having a moisturizer as an effective ingredient and is easily broken by rubbing and in which only a surface portion is formed by a film (in Paragraph [0043], sodium alginate is used), and a gel-type viscous liquid (in Paragraph [0046], carboxy vinyl polymer, DL-alanine, and sodium citrate are used).

(Patent Document 5)

In JP 2-117610 A (Patent Document 5), there is described an emulsion encapsulated capsule-containing cosmetic, the cosmetic containing a capsule encapsulating O/W type emulsion, in which a capsule film is composed of 0.1 to 1.0% by weight of calcium alginate with respect to the total weight of the capsule. The capsule film is formed by reacting water-soluble alginate with a water-soluble calcium salt to purify water-insoluble calcium alginate. In Example 1 of this patent document, there is a description that the capsule film does not remain after using, and in Example 2 of this patent document, in addition to the capsule, a formulation of a cosmetic liquid in which a citric acid and sodium citrate are blended is described.

(Patent Document 6)

In claim 1 of JP 2011-74002 A (Patent Document 6), there is described "A capsule comprising a gel metal salt of Aphanothece sacrum polysaccharide as an outer skin thereof." In claim 2 of this patent document, there is described "The capsule according to claim 1, containing an aqueous solution of a water-soluble component," and based on the description in claim 2, regarding the water-soluble component, there is description in Paragraph [0011] on "amino acids such as arginine, alanine, . . . and salts and derivatives thereof."

Patent Document 1: JP 11-29433 A
Patent Document 2: JP 5-92909 A
Patent Document 3: JP 5-228218 A
Patent Document 4: JP 8-175932 A
Patent Document 5: JP 2-117610 A
Patent Document 6: JP 2011-74002 A

DISCLOSURE OF THE INVENTION

Problem to be Solved by the Invention (As for Patent Document 1 and Patent Documents 2 to 5)
—1—

The invention of Patent Document 1 was made in order to solve limitations and problems of the above Patent Document 5 and the above Patent Documents 2, 3, and 4 relevant to the patent application of the present applicant. In the invention of the capsule-containing cosmetic of Patent Document 1, there is a description that, since a special measure is tried in which the "barium alginate-based capsule A" is caused to be present in the "external solution B composed of the aqueous solution of the pH-adjusted carboxy vinyl polymer," function effects that the capsule A is stably present in the external solution B, the capsule A can be smoothly spread on the skin without film residues when the capsule A is applied to the skin, and the like are exhibited based on synergic action or cooperative action of the barium alginate-based capsule A and the external solution B composed of the aqueous solution of the pH-adjusted carboxy vinyl polymer (see the section "Effect of the Invention" in Paragraphs [0055] to [0060] of this Patent Document 1).
—2—

However, the cosmetic in which the carboxy vinyl polymer is used as the external solution B has limitations or botheration that, for example, (a) an applicable cosmetic is limited to essence or lotion since the thickening property of the carboxy vinyl polymer is high and thus it is inevitable that the system becomes tenacious, (b) although the capsule A itself is softened in the external solution B, the capsule A becomes harder with time in a state where "there is no external solution B" even when the capsule A is accommodated in a container, and thus there is a tendency that a trouble occurs in the application to the skin, and (c) it is necessary to rub the capsule A on the skin with proper time and effort in order not to leave the film when the capsule A is applied to the skin. Therefore, there is a demand for further fundamental improvement.

(As for Patent Document 6)

Patent Document 6 relates to "a capsule comprising a gel metal salt of Aphanothece sacrum polysaccharide as an outer skin thereof," and is considerably different from the present invention and the inventions of Patent Documents 1 to 5 in terms of problems to be solved, solving means, and technical content.

Object of the Invention

Under such a technical background, the present invention is intended to provide a method for producing a soft capsule type external preparation which can be stably stored although being a structural body composed of only a capsule body (C) substantially not having an external solution and does not leave any film residues when rubbed by a finger upon being used as an external preparation, to provide a softening liquid (L) to be used in the producing the same, and to provide a soft capsule type external preparation composed of such a capsule body (C).

Means for Solving Problem

A method for producing a soft capsule type external preparation of the present invention is characterized by including:
bringing an original capsule body (c) in which at least an external surface region in an alginate capsule is present in the form of a polyvalent metal alginate into contact with a softening liquid (L) which is composed of an aqueous solution containing both a basic amino acid (1) and an acid (2) selected from an organic acid or phytic acid so as to impregnate the softening liquid (L) into the original capsule body (c); and thereby obtaining a soft capsule type external preparation composed of an alginate capsule body (C) which does not leave any residues and easily becomes creamy when rubbed with a fingertip.

A softening liquid of the present invention is a softening liquid (L) used for softening an original capsule body (c) in which at least an external surface region in an alginate capsule is present in the form of a polyvalent metal alginate, and the softening liquid is characterized by including:
an aqueous solution containing both a basic amino acid (1) and an acid (2) selected from an organic acid or phytic acid.

A soft capsule type external preparation of the present invention is a soft capsule type external preparation composed of an alginate capsule body (C) and is characterized in that:
both a basic amino acid (1) and an acid (2) selected from an organic acid or phytic acid are impregnated into at least an external surface region in the capsule body (C) from the outside; and
the whole capsule body (C) including the external surface region thereof is formed to be easily broken by rubbing and the whole capsule body (C) does not leave any residues and easily becomes creamy when rubbed with a fingertip.

Effect of the Invention

Regarding the soft capsule type external preparation of the present invention which is composed of the capsule body (C) and is produced as described above using the softening liquid, the capsule body (C) itself can be stably stored (in a state where the capsule body (C) is not impregnated in an external solution, for example). Furthermore, when the capsule body (C) is rubbed by a finger at the time of use as the external preparation, film residues do not remain.

Such a function effect is exhibited based on the synergic action and cooperative action of the "basic amino acid (1)" and the "acid (2) selected from an organic acid or phytic acid" that are two types of components of the softening liquid which is impregnated into at least an external surface region inside the capsule body (C) from the outside.

The external preparations including cosmetics, quasi-drugs, and care products are extremely fine products in which all of performance, image•feeling•whimsy, and usability are demanded. However, the soft capsule type external preparation of the present invention can completely meet such a demand.

BEST MODE(S) FOR CARRYING OUT THE INVENTION

Hereinafter, the present invention will be described in detail.

[Production of Soft Capsule Type External Preparation]
(Preparation of Original Capsule Body (c))
—1—

Upon producing a soft capsule type external preparation of the present invention, first, an original capsule body (c) in which at least an external surface region in an alginate capsule is present in the form of a polyvalent metal alginate is produced. Such an original capsule body (c) can be obtained by a first method or a second method which will be described below.

—2—

The first method for obtaining the original capsule body (c) is a method of making an aqueous solution of a water-soluble salt of alginic acid (a sodium salt or a potassium salt) to be in a state of a small capacity body such as a liquid droplet and bringing the capacity body into contact with an aqueous solution of a water-soluble polyvalent metal salt. In this first method, first, a film of a polyvalent metal alginate polymer is formed on the surface of the "small capacity body (a liquid droplet or the like) of the aqueous solution of the water-soluble salt of alginic acid," and the thickness of the film can be grown (increased) depending on conditions such as temperature, time, concentration, or stirring states.

—3—

Contrary to the above-described method, the second method for obtaining the original capsule body (c) is a method of making an aqueous solution of a water-soluble polyvalent metal salt to be in a state of a small capacity body such as a liquid droplet and bringing the small capacity body into contact with an aqueous solution of a water-soluble salt of alginic acid (a sodium salt or a potassium salt). In this second method, first, a film of a polyvalent metal alginate polymer is formed on the surface of the "small capacity body (a liquid droplet or the like) of the aqueous solution of the polyvalent metal salt," and the thickness of the film can be grown (increased) depending on conditions such as temperature, time, concentration, or stirring states.

—4—

Incidentally, examples of the water-soluble polyvalent metal salt in the first method and the second method include water-soluble calcium salts such as calcium chloride, calcium lactate, and calcium acetate; water-soluble zinc salts such as zinc acetate and zinc lactate; and water-soluble barium salts such as barium chloride, barium acetate, barium lactate, and barium gluconate.

—5—

When the first method and the second method are compared with each other, it is possible to stably achieve the formation of the original capsule body (c) according to the first method, and thus the first method can be said to be generally used.

—6—

In the alginate original capsule body (c) (according to this, also in the capsule body (C)), it is possible to cause an effective ingredient (a medicinal component) to exist. Examples of the effective ingredient (the medicinal component) include various components including moisturizers, vitamins, hormones, glycosides, antihistamine agents, astringents, enzyme agents, isolates from natural animals and plants, oils, dirt adsorbents, pigments, fragrances, protein, carbohydrate, fibers, dyes, and sulfur. The effective ingredient (the medicinal component) may be in a liquid form or a powder form. In the case of a liquid form, an emulsion form of W/O type or O/W type may be employed. In order to prevent transformation of the effective ingredient (the medicinal component), an appropriate UV-cutting agent can also be contained. In addition, various additives including thickening agents, fragrances, colorants, and fillers (titanium oxide, barium sulfate, calcium carbonate, and the like) can also be contained as necessary. The effective ingredient (the medicinal component) present in the original capsule body (c) is also contained in the final capsule body (C).

(Production of Alginate Capsule Body (C))
—1—

Since the original capsule body (c) in which at least an external surface region in an alginate capsule is present in the form of a polyvalent metal alginate is obtained by the first method or the second method described above, a target alginate capsule body (C) is obtained as follows.

—2—

That is, an original capsule body (c) in which at least an external surface region is present in the form of a polyvalent metal alginate is brought into contact with a softening liquid (L) which is composed of an aqueous solution containing both
  a basic amino acid (1) and
  an acid (2) selected from an organic acid or phytic acid
  so as to impregnate the softening liquid (L) into the original capsule body (c).

—3—

The impregnating of the softening liquid (L) into the original capsule body (c) rapidly proceeds at first and gradually becomes slower (see the section of Examples to be described below). Accordingly, the impregnating is generally performed for half a day, 1 day, or several days, for example. Further, it is desirable to set the percentage of the original capsule body (c) and the softening liquid (L) such that substantially whole softening liquid (L) used is impregnated into the original capsule body (c) at the time point when this impregnating operation is finished. If the softening liquid (L) is excessively large, the excessive amount is separated and removed, but it is desirable to set the condition in advance such that there is no need to disposal of the excessive amount since the softening liquid (L) wastes.

—4—

According to the above-described operation, it is possible to obtain a soft capsule type external preparation composed of the alginate capsule body (C) which does not leave any residues and easily becomes creamy when rubbed with a fingertip.

[Softening Liquid (L)]
(Softening Liquid (L))

The softening liquid (L) is an aqueous solution containing both of the "basic amino acid (1)" and the "acid (2) selected from an organic acid or phytic acid," and as necessary, contains various components as described later other than the above-described both acids.

(Basic Amino Acid (1))

—1—

First, an amino acid will be generally described. As being well known, the types of amino acids constituting protein are 20, and the amino acids are classified into three types of a basic amino acid (diaminomonocarboxylic acid), a neutral amino acid (monoaminomonocarboxylic acid), and an acidic amino acid (monoaminodicarboxylic acid) based on chemical structures, isoelectric points, or pH of aqueous solution.

Examples of the basic amino acid include three types of arginine (isoelectric point: 10.76), histidine (isoelectric point: 7.59), and lysine (isoelectric point: 9.75).

Examples of the neutral amino acid include 15 types of glycine, alanine, valine, leucine, isoleucine, serine, threonine, cysteine, methionine, asparagine, glutamine, proline, phenylalanine, tyrosine, and tryptophan. (The isoelectric points of these neutral amino acids are between about 5.1 to about 6.3.)

Examples of the acidic amino acid include aspartic acid (isoelectric point: 2.77) and glutamic acid (isoelectric point: 3.22).

—2—

In order to achieve the object of the present invention, it is necessary to use, as the softening liquid (L), the basic amino acid (1) among the amino acids described above. Arginine (the molecular weight being 174) is a basic amino acid in which the number of Ns is four and the number of COOHs is one. Histidine (the molecular weight being 155) is a basic amino acid in which the number of Ns is three and the number of COOHs is one. Lysine (the molecular weight being 146) is a basic amino acid in which the number of Ns is two and the number of COOHs is one. Among these three types of basic amino acids, arginine is particularly preferable and histidine is also preferable.

Further, the neutral amino acid can be used together with the basic amino acid (1) concurrently, and at this time, an preferred example of the neutral amino acid is alanine.

(Acid (2))

In the present invention, it is necessary to concurrently use the acid (2) selected from an organic acid or phytic acid together with the basic amino acid (1).

Here, citric acid among the acids (2) is suitable for achieving the object of the present invention. The citric acid has a molecular weight of 192 and is oxycarboxylic acid having three COOH groups and one OH group.

As the acid (2), it can be considered that malic acid (oxycarboxylic acid having two COOH groups and one OH group, the molecular weight being 134) and phytic acid (hexanoic acid ester of mesoinosite, the molecular weight being 714) are relatively preferable as well.

As the acid (2), in addition to the above examples, it is also possible to use isocitric acid, glycolic acid, lactic acid, tartaric acid, hydroxy acrylic acid, α-oxybutyric acid, glyceric acid, tartronic acid, aspartic acid (may also be acidic amino acid), glutamic acid (may also be acidic amino acid), acetic acid, succinic acid, malonic acid, oxalic acid, glutaric acid, phthalic acid, isophthalic acid, ascorbic acid, gluconic acid, fumaric acid, or benzoic acid.

(Quantitative Ratio of Basic Amino Acid (1) and Above-Described Acid (2))

The quantitative ratios of the basic amino acid (1) and the above-described acid (2) in the softening liquid (L) are considerably different depending on the kinds thereof and the method of combining the basic amino acid (1) and the acid (2) as in Experimental Examples to be described later, and thus cannot be identically decided. However, when a case where the basic amino acid (1) is arginine and the above-described acid (2) is citric acid is considered as an example, it is appropriate that a molar ratio of arginine/citric acid is set to be in the range of about 1 to 20. The point is that it should be paid attention to prevention of a case where a property in which the capsule body (C) to be obtained is easily broken by rubbing is impaired since the capsule body (C) is excessively swollen so as to be dissolved or is insufficiently swollen so as to be too hard.

(Other Components)

The softening liquid (L) may contain components exhibiting an action of a moisturizer, a preservative, or the like in addition to each component described above. In Experimental Examples to be described later, as a moisturizer which is also used as a preservative, a case where three components of 1,2-hexanediol, butylene glycol, and pentylene glycol are used concurrently and blended is presented.

(Ratio of Original Capsule Body (c) and Softening Liquid (L))

The ratio of the original capsule body (c) and the softening liquid (L) is selected from the range of 2:8 to 7:3 in terms of weight ratio in many cases, but this range is merely a rough standard. It is sufficient that the hardness of the final capsule body (C) is in the preferred range as described later by the impregnating of the softening liquid (L) into the original capsule body (c).

[Soft Capsule Type External Preparation Composed of Capsule Body (C)]

(Aspect of Capsule Body (C))

A target alginate capsule body (C) is produced by impregnating the softening liquid (L) into the original capsule body (c) as described above. The whole capsule body (C) including the external surface region thereof is formed to be easily broken by rubbing and the whole capsule body (C) does not leave any residues and easily becomes creamy when rubbed with a fingertip.

(Hardness of Capsule Body (C))

The hardness of this capsule body (C) (the hardness at the stage in which the capsule body (C) is disposed as a product in the market) is smaller than the hardness of the original capsule body (c) and is set to the range in which the shape thereof is maintained. For example, the hardness is set to be 500 g or less and preferably 450 g or less at the compressive strength by RHEO METER to be described later.

(Shape of Capsule Body (C))

The shape of the capsule body (C) is a spherical shape in many cases, but it is possible to produce the capsule body (C) having various non-spherical shapes including a tear shape, a barrel shape, a magatama shape, a dice shape, a star shape, a character shape, a flower shape, a nut shape, a fruit shape, a vegetable shape, and an animal shape by forming the original capsule body (c) using a mold as necessary, and then bringing the original capsule body (c) into contact with the softening liquid (L).

(Size of Capsule Body (C))

The size of the capsule body (C) (being a little over one time to about 30 times the original capsule body (c) in terms of volume as compared with the original capsule body (c) described above) is not particularly limited, but when the case of a spherical shape is considered as an example, in many cases, the diameter is about 0.1 to 20 mm, generally about 0.5 to 10 mm, and particularly about 1 to 8 mm.

(Use of Capsule Body (C))

The soft capsule type external preparation of the present invention composed of the capsule body (C) can be used as a cosmetic for bath, health, sports, or the like in addition to general cosmetics. In addition, the soft capsule type external preparation can be also used as a quasi-drug, a care product, or the like.

(Product Form)

Further, the soft capsule type external preparation of the present invention composed of the capsule body (C) is put on the market in a state where the soft capsule type external preparation is accommodated in an appropriate container such as a jar, a bottle, or a tube. For extracting the soft capsule type external preparation from the container, a spoon may be used in many cases, but an extruding type can be also employed.

EXAMPLES

Next, the present invention will be described in more detail by means of Examples (Experimental Examples). Evaluation on hardness of the capsule body (C) in Tables 1 to 7 is conducted based on four grades of "⊙>○>□>x" in the order from the preferred evaluation result.

Experimental Example 1

Preparation of Original Capsule Body (c)

16 parts by weight of an aqueous solution of 5.0% by weight of sodium alginate blended with 10 parts by weight of ester oil as an example of an effective ingredient was prepared, and water was further added thereto under stirring such that the entire solution became 100 parts by weight.

This aqueous solution was added dropwise to a large amount of receiving liquid composed of an aqueous solution of 1% by weight of calcium chloride from a nozzle. The mixed solution was stirred so as to form capsules, and these capsules were scooped up, and then put into water and washed. According to this, pearl-shaped white original capsule bodies (c) having a particle diameter of about 3 mm were obtained. At least an external surface side of the original capsule body (c) was formed by calcium alginate. When this original capsule body (c) is attached to the skin and is rubbed by a finger, film residues slightly remain. In Experimental Examples to be described below, the original capsule bodies (c) having a particle diameter of 3 mm±0.5 mm among the obtained original capsule bodies (c) were subjected to screening and then used.

(Preparation of Capsule Body (C) by Impregnating Softening Liquid (L) and Hardness Thereof)

—1—

First, an aqueous solution obtained by dissolving the "arginine as the basic amino acid (1)," "alanine as the neutral amino acid," and "citric acid or glutamic acid as the acid (2)" in purified water was prepared such that concentrations thereof became the concentrations in Tables to be described later. Further, 10.5 parts by weight of diol-based and triol-based moisturizers were dissolved in 27.5 parts by weight of this aqueous solution to prepare 38 parts by weight of swelling liquid. Subsequently, 38 parts by weight of this swelling liquid was further diluted with 12 parts by weight of purified water to prepare 50 parts by weight of the softening liquid (L). In the experiment below, the original capsule body (c) was put into 50 parts by weight of this softening liquid (L) so as to perform softening.

—2—

The original capsule body (c) was put into the softening liquid (L) with the formulation of Experiment No. 3 in Table 1 to be described later, and then the capsule body (C) was extracted at stages after lapses of 0.25 hour, 0.5 hour, 0.75 hour, 12 hours, and 72 hours. The hardness thereof (the average value of ten capsule bodies (C)) was measured and thus the following results were obtained. The diameter of the capsule body (C) after a lapse of 12 hours was about 1.3 times the diameter of the original capsule body (c). (Incidentally, in this state, even when the capsule body (C) was put into a container, a cover was put on the container, and then the capsule body (C) was stored for a long period of time, the particle shape was maintained.)

| | |
|---|---|
| Hardness after a lapse of 0.25 hour | 728 g |
| Hardness after a lapse of 0.5 hour | 659 g |
| Hardness after a lapse of 0.75 hour | 627 g |
| Hardness after a lapse of 12 hours | 279 g |
| Hardness after a lapse of 72 hours (after 3 days) | 187 g |

—3—

Incidentally, the measurement of the hardness was performed using "SUN RHEO METER: COMPAC-100II" manufactured by SUN SCIENTIFIC CO., LTD. according to the following procedures.

1: A syringe (for tuberculin, 1 mL) and a needle for dropwise addition are prepared.

2: The piston of the syringe is pulled out.

3: The syringe is filled with about 10 capsule bodies (C) describe above from the rear portion of the syringe.

4: The needle is equipped to the syringe, the piston is equipped, the capsule body (C) is pushed to push the capsule such that a trace amount thereof is taken out from the needle, and thus the capsule body (C) is filled in the middle of the needle.

5: The syringe is set to a table in the vertical direction, and then measurement is performed at a setting value of 10 mm and a measuring speed of 60 mm/min.

—4—

From the result of this preliminary experiment, it was found that the softening of the film at the external surface side of the original capsule body (c) rapidly proceeded within an initial several hours after the original capsule body (c) was put into the softening liquid (L), and then the softening became slower and approached to a constant value over a long time period. For this reason, hereinafter, regarding experiments on various formulations, experiments on various formulations of the capsule body (C) when taken out after a lapse of 12 hours were performed. The conditions and results thereof are shown in the following Table 1 and Table 2.

TABLE 1

| Experiment No. | p Arginine (% by weight) | Alanine (% by weight) | q Citric acid (% by weight) | p/q molar ratio | Hardness (g) and evaluation of capsule body (C) | |
|---|---|---|---|---|---|---|
| 5 | — | — | — | | Non-swollen | X |
| 15 | 1.56 | — | — | | Non-swollen | X |
| 4 | 1.56 | 2.03 | — | | Non-swollen | X |
| 14 | 1.56 | 2.03 | — | | Non-swollen | X |
| 2 | — | — | 0.67 | | Non-swollen | X |
| 1 | 1.56 | — | 0.67 | 2.6 | 300 | ⊙ |
| 3 | 1.56 | 2.03 | 0.67 | 2.6 | 279 | ⊙ |
| 13 | 1.56 | 2.03 | 0.67 | 2.6 | 213 | ⊙ |

TABLE 1-continued

| Experiment No. | p Arginine (% by weight) | Alanine (% by weight) | q Citric acid (% by weight) | p/q molar ratio | Hardness (g) and evaluation of capsule body (C) | |
|---|---|---|---|---|---|---|
| 6 | 1.56 | 0.20 | 0.67 | 2.6 | 300 | ⊙ |
| 7 | 1.56 | 0.41 | 0.67 | 2.6 | 227 | ⊙ |
| 8 | 1.56 | 1.02 | 0.67 | 2.6 | 299 | ⊙ |
| 9 | 1.56 | 1.52 | 0.67 | 2.6 | 306 | ⊙ |
| 17 | 1.56 | — | 0.33 | 5.4 | 272 | ⊙ |
| 12 | 0.78 | 2.03 | 0.67 | 1.3 | 505 | ○ |
| 18 | 1.56 | — | 0.07 | 25.0 | 627 | □ |
| 10 | 0.16 | 2.03 | 0.67 | 0.26 | Non-swollen | X |
| 11 | 0.31 | 2.03 | 0.67 | 0.5 | Non-swollen | X |

Note 1:
Arginine is a representative example of the basic amino acid.
Note 2:
Alanine is a representative example of the neutral amino acid.
Note 3:
Citric acid is a representative example of the organic acid.
Note 4:
In Experiment Nos. 3 and 13 and Experiment Nos. 4 and 14, the same conditions are repeated.

TABLE 2

| Experiment No. | p Arginine (% by weight) | Alanine (% by weight) | r Glutamic acid (% by weight) | p/r molar ratio | Hardness (g) and evaluation of capsule body (C) | |
|---|---|---|---|---|---|---|
| 16 | 1.56 | — | 0.67 | 2.0 | Non-swollen | X |
| 19 | 1.56 | — | 1.00 | 1.3 | Non-swollen | X |

Note 1:
Glutamic acid is an example of the organic acid.

(Consideration)
From the results shown in the above Tables 1 and 2, the following matters are found.
 As Experiment No. 5 in Table 1, when the softening liquid (L) lacks both of the basic amino acid (1) and the acid (2), the softening cannot be performed.
 In Experiment Nos. 15, 4, and 14 in Table 1, since the acid (2) as a counterpart (opposing part) is lacked although arginine is used as the basic amino acid (1), it is not possible to achieve the object of the softening.
 As Experiment No. 2 in Table 1, when the component of the softening liquid is only citric acid as the acid (2) and arginine as the basic amino acid (1) is lacked, it is not possible to achieve the object of the softening.
 As Experiment Nos. 1, 3, 13, 6, 7, 8, 9, and 17 in Table 1, when the combination of arginine as the basic amino acid (1) and citric acid as the acid (2) is used and the amount ratio of both components is proper, the softened capsule body (C) with an evaluation result of ⊙ is obtained.
 In Experiment No. 12 in Table 1, since the molar ratio of arginine/citric acid is slightly small although the combination of arginine and citric acid is used, the evaluation result of ○ is obtained.
 In Experiment No. 18 in Table 1, since the molar ratio of arginine/citric acid tends to be extremely large although the combination of arginine and citric acid is used, the evaluation result of □ is obtained.
 On the other hand, in Experiment Nos. 10 and 11 in Table 1, since the molar ratio of arginine/citric acid exceeds the limit and is too small although the combination of arginine and citric acid is used, the evaluation result of x is obtained.
 When Experiment Nos. 10 and 11 in Table 1 and Experiment No. 18 in Table 1 are compared with each other, regarding the relation between arginine and citric acid, the softening properly proceeds in Experiment No. 18 in which the amount of citric acid is decreased; however, almost no softening proceeds in Experiment Nos. 10 and 11 in which the amount of arginine is decreased. From this matter, it is found that arginine has a greater influence on the softening than citric acid.
 In Experiment Nos. 16 and 19 in Table 2, glutamic acid is used as the acid (2) instead of citric acid, but the softening is not achieved. It is found that citric acid as shown in Table 1 is suitable for the acid (2) serving as the counterpart (opposing part) of arginine as the basic amino acid (1).

Experimental Example 2

An original capsule body (c) was prepared in the same manner as in Experimental Example 1, and the original capsule body (c) was softened by using the softening liquid (L) having the same formulation as in Experimental Example 1, thereby obtaining a capsule body (C). The conditions and results are shown in the following Table 3, Table 4, and Table 5.

TABLE 3

| Experiment No. | p Arginine (% by weight) | Alanine (% by weight) | q Citric acid (% by weight) | p/q molar ratio | Hardness (g) and evaluation of capsule body (C) | |
|---|---|---|---|---|---|---|
| 20A | 4.1 | 5.35 | 1.75 | 2.6 | 250 | ⊙ |
| 20 | 4.1 | 5.35 | 0.88 | 5.1 | 306 | ⊙ |
| 21 | 4.1 | 5.35 | 0.18 | 25 | Non-swollen | X |
| 30 | 2.05 | 5.35 | 1.75 | 1.3 | 411 | ⊙~○ |

TABLE 4

| Experiment No. | p Arginine (% by weight) | Alanine (% by weight) | s Malic acid (% by weight) | p/s molar ratio | Hardness (g) and evaluation of capsule body (C) | |
|---|---|---|---|---|---|---|
| 25 | 4.1 | 5.35 | 3.5 | 0.9 | 300 | ⊙ |
| 22 | 4.1 | 5.35 | 1.75 | 1.8 | 330 | ⊙ |
| 23 | 4.1 | 5.35 | 0.88 | 3.6 | Non-swollen | X |
| 24 | 4.1 | 5.35 | 0.18 | 18 | Non-swollen | X |

TABLE 5

| Experiment No. | p Arginine (% by weight) | Alanine (% by weight) | t Phytic acid (% by weight) | p/t molar ratio | Hardness (g) and evaluation of capsule body (C) | |
|---|---|---|---|---|---|---|
| 26 | 4.1 | 5.35 | 1.75 | 9.6 | 219 | ○ |
| 27 | 4.1 | 5.35 | 0.88 | 20 | Dissolved | X |

TABLE 5-continued

| Experiment No. | p Arginine (% by weight) | Alanine (% by weight) | t Phytic acid (% by weight) | p/t molar ratio | Hardness (g) and evaluation of capsule body (C) | |
|---|---|---|---|---|---|---|
| 28 | 4.1 | — | 5.35 | 0.44 | 39 | 228 ⊙ |
| 29 | 4.1 | — | 5.35 | 0.09 | 182 | Non-swollen X |

Experimental Example 3

An original capsule body (c) was prepared in the same manner as in Experimental Example 1, and the original capsule body (c) was softened by using the softening liquid (L) having the same formulation as in Experimental Example 1, thereby obtaining a capsule body (C). The conditions and results are shown in the following Table 6.

TABLE 6

| Experiment No. | u Histidine (% by weight) | Alanine (% by weight) | q Citric acid (% by weight) | u/q molar ratio | Hardness (g) and evaluation of capsule body (C) | |
|---|---|---|---|---|---|---|
| 31 | 4.1 | — | 1.75 | 2.9 | 212 | ⊙ |
| 32 | 4.1 | — | 1.75 | 2.9 | 218 | ⊙ |
| 33 | 2.05 | — | 1.75 | 1.45 | Non-swollen | X |

Note 1:
In Experiment Nos. 31 and 32, the same conditions are repeated.

(Consideration)

From the results shown in the above Table 6, the following matters are found.

When Experiment No. 20A and Experiment No. 30 in Table 3 using both of arginine and citric acid were compared with each other, it was found that the allowable range of the used amount of histidine is slightly narrow in the histidine-citric acid type in Table 6 using histidine instead of arginine. However, it was found that, if attention is paid to the used amount of histidine, the same preferable result as in the case of using arginine is obtained.

INDUSTRIAL APPLICABILITY

According to the present invention, it is possible to produce a target capsule body (C) by bringing the original capsule body (c) into contact with a specific softening liquid (L). The soft capsule type external preparation of the present invention which is composed of the obtained capsule body (C) is useful as an external preparation including a cosmetic, a quasi-drug, and a care product.

The invention claimed is:

1. A method for producing a soft capsule type external preparation, the method comprising:
    bringing an original capsule body (c) in which at least an external surface region in an alginate capsule is present in the form of a polyvalent metal alginate into contact with a softening liquid (L) which is composed of an aqueous solution containing both a basic amino acid (1) and an acid (2) selected from an organic acid or phytic acid so as to impregnate the softening liquid (L) into the original capsule body (c); and
    thereby obtaining a soft capsule external preparation composed of an alginate capsule body (C) which does not leave any residues and easily becomes creamy when rubbed with a fingertip.

2. The production method according to claim 1, wherein the basic amino acid (1) is at least one basic amino acid selected from the group consisting of arginine and histidine.

3. The production method according to claim 1, wherein the acid (2) is at least one acid selected from the group consisting of citric acid, malic acid, and phytic acid.

4. A soft capsule external preparation comprising an alginate capsule body (C), wherein
    both a basic amino acid (1) and an acid (2) selected from an organic acid or phytic acid are present in at least an external surface region in the capsule body (C), and
    the whole capsule body (C) including the external surface region thereof is formed to be easily broken by rubbing and the whole capsule body (C) does not leave any residues and easily becomes creamy when rubbed with a fingertip.

* * * * *